United States Patent
Spence

(10) Patent No.: US 9,504,773 B2
(45) Date of Patent: *Nov. 29, 2016

(54) METHODS AND SYSTEMS FOR COUNTERPULSATION OF BLOOD FLOW TO AND FROM THE CIRCULATORY SYSTEM

(71) Applicant: Paul A. Spence, Louisville, KY (US)

(72) Inventor: Paul A. Spence, Louisville, KY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/792,651

(22) Filed: Jul. 7, 2015

(65) Prior Publication Data

US 2015/0306289 A1   Oct. 29, 2015

Related U.S. Application Data

(63) Continuation of application No. 14/157,132, filed on Jan. 16, 2014, now Pat. No. 9,095,649, which is a continuation of application No. 13/778,835, filed on Feb. 27, 2013, now Pat. No. 8,663,085, which is a
(Continued)

(51) Int. Cl.
*A61M 1/12* (2006.01)
*A61M 1/10* (2006.01)

(52) U.S. Cl.
CPC ........... *A61M 1/1005* (2014.02); *A61M 1/106* (2013.01); *A61M 1/107* (2013.01); *A61M 1/1008* (2014.02); *A61M 1/1044* (2014.02); *A61M 1/1086* (2013.01); *A61M 1/122* (2014.02); *A61M 1/127* (2013.01)

(58) Field of Classification Search
CPC .. A61M 1/10; A61M 1/1001; A61M 1/1005; A61M 1/1008; A61M 1/106; A61M 1/107; A61M 1/122

USPC ..................................................... 600/16–18
See application file for complete search history.

(56) References Cited

U.S. PATENT DOCUMENTS

| | | |
|---|---|---|
| 2,935,068 A | 5/1960 | Donaldson |
| 3,195,540 A | 7/1965 | Waller |
| 3,942,535 A | 3/1976 | Schulman |
| 4,014,317 A | 3/1977 | Bruno |
| 4,080,958 A | 3/1978 | Bregman et al. |
| 4,116,589 A | 9/1978 | Rishton |
| 4,790,825 A | 12/1988 | Bernstein et al. |

(Continued)

FOREIGN PATENT DOCUMENTS

| | | |
|---|---|---|
| WO | 97/42413 A1 | 11/1997 |
| WO | 99/59652 A1 | 11/1999 |
| WO | 01/80927 A2 | 11/2001 |

OTHER PUBLICATIONS

John N. Nanas et al., A Valveless High Stroke Volume Counterpulsation Device Restores Hemodynamics in Patients with Congestive Heart Failure and Intractable Cardiogenic Shock Awaiting Heart Transplantation, The Journal of Thoracic and CardiovascularSurgery, pp. 55-61, Athens, Greece, Jan. 1996.
(Continued)

*Primary Examiner* — Allen Porter, Jr.

(57) ABSTRACT

Counterpulsation methods and systems for assisting the heart of a patient involve, for example, coordinating the operation of a pulsatile pump to suction blood from an artery through a blood flow conduit while the heart is in systole and expel the blood into the blood flow conduit and the artery while the heart is in diastole.

6 Claims, 11 Drawing Sheets

Related U.S. Application Data continuation of application No. 13/309,637, filed on Dec. 2, 2011, now Pat. No. 8,388,511, which is a continuation of application No. 12/827,227, filed on Jun. 30, 2010, now Pat. No. 8,092,364, which is a continuation of application No. 11/841,244, filed on Aug. 20, 2007, now Pat. No. 7,766,813, which is a continuation of application No. 10/978,876, filed on Nov. 1, 2004, now Pat. No. 7,273,446.

(60) Provisional application No. 60/516,529, filed on Oct. 31, 2003.

(56) References Cited

U.S. PATENT DOCUMENTS

| | | | |
|---|---|---|---|
| 4,994,078 | A | 2/1991 | Jarvik |
| 4,995,857 | A | 2/1991 | Arnold |
| 5,171,207 | A | 12/1992 | Whalen |
| 5,171,218 | A | 12/1992 | Fonger et al. |
| 5,190,528 | A | 3/1993 | Fonger et al. |
| 5,290,227 | A | 3/1994 | Pasque |
| 5,344,385 | A | 9/1994 | Buck et al. |
| 5,344,443 | A | 9/1994 | Palma et al. |
| 5,545,191 | A | 8/1996 | Mann et al. |
| 5,653,676 | A | 8/1997 | Buck et al. |
| 5,695,471 | A | 12/1997 | Wampler |
| 5,701,919 | A | 12/1997 | Buck et al. |
| 5,704,891 | A | 1/1998 | Mussivand |
| 5,711,753 | A | 1/1998 | Pacella et al. |
| 5,738,649 | A | 4/1998 | Macoviak |
| 5,741,316 | A | 4/1998 | Chen et al. |
| 5,743,845 | A | 4/1998 | Runge |
| 5,840,070 | A | 11/1998 | Wampler |
| 5,858,009 | A | 1/1999 | Jonkman |
| 5,904,666 | A | 5/1999 | DeDecker et al. |
| 5,924,848 | A | 7/1999 | Izraelev |
| 5,924,975 | A | 7/1999 | Goldowsky |
| 5,938,412 | A | 8/1999 | Izraelev |
| 5,941,813 | A | 8/1999 | Sievers et al. |
| 5,947,892 | A | 9/1999 | Benkowski et al. |
| 5,948,006 | A | 9/1999 | Mann |
| 5,965,089 | A | 10/1999 | Jarvik et al. |
| 5,984,857 | A | 11/1999 | Buck et al. |
| 6,132,363 | A | 10/2000 | Freed et al. |
| 6,299,575 | B1 | 10/2001 | Bolling |
| 6,428,464 | B1 | 8/2002 | Bolling |
| 6,471,633 | B1 | 10/2002 | Freed |
| 6,511,412 | B1 | 1/2003 | Freed et al. |
| 6,530,876 | B1 | 3/2003 | Spence |
| 6,579,223 | B2 | 6/2003 | Palmer |
| 6,770,024 | B1 | 8/2004 | Rastegar et al. |
| 6,889,082 | B2 | 5/2005 | Bolling et al. |
| 2002/0151761 | A1 | 10/2002 | Viole et al. |
| 2002/0173693 | A1 | 11/2002 | Landesberg |
| 2003/0069468 | A1 | 4/2003 | Bolling et al. |
| 2003/0088147 | A1 | 5/2003 | Bolling et al. |
| 2003/0139643 | A1 | 7/2003 | Smith et al. |
| 2003/0176760 | A1 | 9/2003 | El Oakley et al. |
| 2004/0116769 | A1 | 6/2004 | Jassawalla et al. |
| 2004/0147803 | A1 | 7/2004 | Hegde et al. |

OTHER PUBLICATIONS

R. J. Baird et al., Le Support Mchanique Du Ventricule Gauche, L'Union Med. du Canada, Tome 93, pp. 258-268, Dec. 1964.

R.J. Baird et al., Survey of Mechanical Assistance of the Circulation and the Present Status of Left-Heart Bypass, Mechanical Support of the Circulation, Department of Surgery, Univ. of Toronto, pp. 340-345, 1965.

World Heart Corporation, World Heart, 1998 Annual Report.

Richard P. Cochran et al., Ambulatory Intraaortic Balloon Pump Use as Bridge to Heart Transplant, Division of Cardiothoracic Surgery, University of Wisconsin, Madison, Wisconsin, Ann Thorac Surg vol. 74, pp. 746-752, 2002.

Valluvan Jeevanadam et al., Circulatory Assistance with a Permanent Implantable IABP: Initial Human Experience, Circulation, vol. 106, pp. 1-183-1-188, 2002.

Arrow International, Inc., AutoCAT(TM)2WAVE, Brochure, Arrow International, Inc. USA, 2003.

Datascope, The CS100(TM) Intelligent Counterpulsation, Brochure, 2003.

John N. Nanas et al., Comparison of an Implanted Abdominal Aortic Counterpulsation Device with the Intraaortic Balloon Pump in a Heart Failure Model, Salt Lake City, Utah, J Am College Cardiology, vol. 7, pp. 1028-1035, 1986.

John N. Nanas et al., Effectiveness of a Counterpulsation Device Implanted on the Ascending Aorta, Trans Am Soc Artif Intern Organs, vol. 33, pp. 203-206, 1987.

John N. Nanas et al., Hemodynamic Effects of a Counterpulsation Device Implanted on the Ascending Aorta in Severe Cardiogenic Shock, Trans Am Soc Artif Intern Organs, vol. 34, pp. 229-234, 1988.

Jeffrey D. Manord et al., Implications for the Vascular Surgeon with Prolonged (3 to 89 days) Intraaortic Balloon Pump Counterpulsation, J Vasc Surg., vol. 26, pp. 511-516, Sep. 1997.

Alan M. Rosenbaum et al., Intra-aortic Balloon Counterpulsation as a 'Bridge' to Cardiac Transplantation, Chest, vol. 106, pp. 1683-1688, Dec. 1994.

Jeanny K. Park et al., Intraaortic Balloon Pump Management of Refractory Congestive Heart Failure in Children, Pediatric Cardiology, vol. 14, No. 1, pp. 19-22, 1993.

Paul S. Freed et al., Intraaortic Balloon Pumping for Prolonged Circulatory Support, The American Journal of Cardiology, vol. 61, pp. 554-557, Mar. 1, 1988.

John N. Nanas et al., Preclinical Evaluation of the Abdominal Aortic Counterpulsation Device, American Heart Journal, pp. 1003-1008, Salt Lake City, Utah, Oct. 1998.

John V. Terrovitis et al., Superior Performance of a Paraaortic Counterpulsation Device Compared to the Intraaortic Balloon Pump, University of Athens School of Medicine, Department of Clinical Therapeutics, Alexandra Hospital, Athens, Greece,website, www.springerlink.com, World Journal of Surgery, 17 pgs., Nov. 5, 2003.

METHODS AND SYSTEMS FOR COUNTERPULSATION OF BLOOD FLOW TO AND FROM THE CIRCULATORY SYSTEM

CROSS-REFERENCE TO RELATED APPLICATIONS

This application is a continuation of application Ser. No. 14/157,132, filed Jan. 16, 2014 which is a continuation of application Ser. No. 13/778,835, filed Feb. 27, 2013 (now U.S. Pat. No. 8,663,085), which is a continuation of application Ser. No. 13/309,637, filed Dec. 2, 2011 (now U.S. Pat. No. 8,388,511), which is a continuation of application Ser. No. 12/827,227, filed Jun. 30, 2010 (now U.S. Pat. No. 8,092,364) which is a continuation of application Ser. No. 11/841,244, filed Aug. 20, 2007 (now U.S. Pat. No. 7,766,813) which is a continuation of application Ser. No. 10/978,876, filed Nov. 1, 2004 (now U.S. Pat. No. 7,273,446) which claims the benefit of U.S. Provisional Application No. 60/516,529 filed on Oct. 31, 2003, the disclosures of which are hereby incorporated by reference herein.

BACKGROUND OF THE INVENTION

Congestive heart failure is a major problem in today—over 5 million patients in the U.S. and probably even more in the EU are afflicted. There is no effective medication to improve the strength of heart contraction and to date there has been little advancement toward solving this problem on a mass scale. Attempts should be directed to a simple, proven and minimally invasive system to help these patients.

Aortic counterpulsation is a well-established form of assistance for a failing heart. In one type of counterpulsation procedure, as the heart ejects blood in systole, blood is removed from the aorta thus relieving the work of the heart in ejecting blood. As the heart relaxes in diastole, the removed blood is pumped back into the aorta increasing the blood pressure and flow to the organs. This assists the heart for two reasons. First, the work on the heart is reduced because blood is withdrawn from the aorta as the heart is working (cardiac unloading). Second, the heart is unusual among organs in that most of its perfusion occurs during diastole so that higher pressures during diastole cause a major improvement to the flow of blood in the heart. Improved perfusion and oxygenation of the heart and reduced work performed by the heart typically result in improved performance of the heart and improved circulation for the entire body. Many patients have been saved from certain death by application of this concept. Failing hearts and vital organs such as kidneys are frequently resuscitated by this method.

Most commonly, counterpulsation is achieved with a balloon inside the aorta rather than actually removing blood and returning blood to the aorta. This device is known as the intraaortic balloon pump. In practice a patient receives a balloon mounted (usually about 40 ml in size) on a catheter (1-2 m long). The catheter is introduced into the patient via a groin artery. The balloon resides in the descending aorta (beyond the take-off of the vessels to the head and neck). The balloon is deflated in systole to help the heart eject (rather than remove the blood) and inflated in diastole (rather than return the blood). The balloon is inflated and deflated by gas (usually helium) which is shuttled in and out of the catheter. The passage of the gas is driven and controlled by a console which times or coordinates the movement of gas with the patient's EKG to ensure that the optimal timing of the inflation and deflation occurs to ensure maximal improvement in cardiac performance results.

The intraaortic balloon pump has a number of major drawbacks. First, it is almost always inserted by a puncture in a major groin artery. The patient must remain supine in bed. Movement is extremely limited as movement on the catheter may cause bleeding from the artery which has been punctured. Patients often deteriorate while supine as muscles weaken from inactivity and the risk of pneumonia and leg clots increases.

Infection is also a major concern. The catheter travels out of the groin artery of the patient. Any catheter tracking into the body tends to become colonized with bacteria. Over time the bacteria travel up the catheter and into the blood stream. As the groin area is plentiful with bacteria, this area is particularly ripe for the origin of infection.

Another concern is that of limb ischemia. The catheter may be close to the size of the patients groin artery and may occlude the flow of blood to the leg and risking the loss of that limb. Even when the groin arteries are large, over time clotting tends to occur around the catheter and flow becomes reduced to the limb beyond the entry site. After a number of days there is an increasing risk of leg ischemia and leg loss.

In clinical practice, an intraaortic balloon pump usually remains in place just a day or two. If it is left more than about a week, the doctors become extremely concerned that a serious complication will occur and typically remove the balloon.

Many patients have chronically weakened hearts that require long-term support. Despite the fact that counterpulsation is extremely helpful to these patients, there has been no way to apply this technology practically for a long period of time (i.e., months or years). It would be very valuable for patients to have a system that provides counterpulsation but does not carry the risks of the intraaortic balloon pump.

Furthermore, these patients are very ill and cannot tolerate major procedures. An attempt has been described to perform long-term counterpulsation by opening the patient's chest and then sewing a balloon pouch inside the aorta. This pouch is then attached to a drive line. Initial studies suggest that this does indeed provide considerable long term help to a failing heart. However, it is unlikely that this procedure could ever be used on a large scale as it is so invasive. In another approach, the counterpulsation pouch has been sewn to the thoracic or abdominal aorta. However, this requires a major procedure—a thoracotomy or a laparotomy to gain entry to the chest or abdominal cavity.

Blood pumps have also been used to assist the failing heart. In general, blood is taken from the left atrium or left ventricle and then pumped into the aorta. This form of cardiac assist is extremely effective. However, there are a number of problems that have not been satisfactorily solved and this technology is not yet widely used in heart failure. The first problem is that insertion of these devices requires a major procedure for connection to the heart and the aorta. The pumps have blood contacting surfaces, particularly bearings, and these are prone to clotting. Clots may either break loose and embolize (migrate) to the body causing strokes or other organ problems or may stay in place and enlarge to the point that they cause the device to malfunction. The systems also contain valves which regulate the direction of flow in the system. These valves, in combination with stasis points within the system may also contribute to clotting. Another major problem with these devices is that they require major regulation. It is never clear how much blood should be pumped. If too little is pumped, the patient suffers from insufficient circulation. If the pump is set too high, the heart can be sucked flat and then drawn into the pump with serious consequences to the heart. Patients in heart failure have considerable variation over time in the fluid volume of their hearts and the flow rates in the circulation. If the pump does not precisely respond to these variations, failure may occur.

Counterpulsation eliminates many of the problems with blood pumping. There is no necessity for pump bearing-to-blood contact as the blood can fill and empty from a blood sac insulated from the driving pump or device. No valves are necessary. Stasis is minimal as the blood fills and empties completely from the blood sac on each cardiac cycle. Perhaps most important is that the regulation of this device is simple. The system is not connected directly to the heart. Thus it can fill and empty each cycle without the need to adjust the volume that is pumped by the system.

In summary, aortic counterpulsation is a proven form of heart assist in acute and chronic heart failure. Unfortunately, no chronic form has been developed that can be provided to the patient in a minor procedure, allows mobility and reduces the risk of long term infection. Such a system would be very useful to the millions of patients suffering from congestive heart failure.

SUMMARY

In one embodiment, the present invention provides a counterpulsation method of assisting the heart of a patient using a pump assist system with the method comprising coupling a first conduit to the arterial system of the patient without entering the chest cavity or abdominal cavity of the patient. A pulsatile pump is connected to the first conduit and the pump is implanted in the patient without entering the chest cavity or abdominal cavity of the patient. The power supply is connected to the pump and the operation of the pump is coordinated to suction blood from the arterial system through the first conduit while the heart is in systole and expel the blood into the first conduit and the arterial system while the heart is in diastole. The power supply may be mounted within the patient's body, outside the patient's body, or with respective portions of the power supply system located inside and outside the body.

The method can further include coupling a second conduit to the first conduit, and coupling the second conduit to the arterial system without entering the chest cavity or the abdominal cavity of the patient. Again the pulsatile pump operation is coordinated to suction blood from the arterial system through the first and second conduits while the heart is in systole and expel the blood into the arterial system while the heart is in diastole. Coupling the first and second conduits to the arterial system can further comprise coupling the first and second conduits to different arteries in the system. Another option is to couple the first and second conduits to the same artery. It will be appreciated that the conduit(s) may be preconnected to the pump.

In accordance with another aspect or embodiment of the invention, the method can further include connecting a second, continuous pump to the patient for purposes of assisting blood flow from the heart. This may be accomplished by directing another conduit into the left side of the heart, and yet another conduit to the arterial system of the patient. A continuous pump is connected between these conduits, and preferably implanted in the patient. A power supply, which may be the same as, coupled with, or different from the power supply for the pulsatile pump, is connected to the continuous pump. The method then further includes suctioning blood from the left side of the heart by way of the continuous pump and expelling the blood into the arterial system of the patient.

The conduit or conduits of the invention may be coupled to a superficial, subcutaneous artery of the patient, such as one or more arteries in the neck, shoulder or upper chest region of the patient. Alternatively, the artery may be located in the retroperitoneal region of the patient, such as the distal aorta, iliac, external iliac, internal iliac or femoral artery systems. The pump may be, for example, implanted in the pelvic region and, more specifically, even in the retroperitoneal region. Although this latter location would be somewhat more invasive than, for example, a superficial region of the chest, it is still much less invasive than intraabdominal or intrathoracic procedures. A direct connection to the aorta may be accomplished with one or more conduits, and with the pump located in the superficial upper chest region similar to a pacemaker. Again, although the connection to the aorta is invasive, the superficial location of the pump makes the overall procedure much less invasive than conventional invasive procedures and less traumatic to the patient.

In another embodiment, the method includes coupling a first conduit to the arterial system without entering the chest cavity or abdominal cavity of the patient, coupling a second conduit to the arterial system of the patient without entering the chest cavity or abdominal cavity of the patient, and connecting a pump between the first and second conduits. The pump suctions blood from the arterial system through the first conduit and expels the blood into the arterial system. As one option, the pump may expel blood through both the first and second conduits while in another option, the blood may be expelled from the pump through only the second conduit through the use, for example, of appropriate valving.

In another embodiment of the method, the pump is implanted in the patient without entering the chest cavity or abdominal cavity of the patient and the first conduit is coupled to the arterial system and to the pump. The coupling of the first conduit to the arterial system may, in this embodiment, be through a superficial, subcutaneous connection or a more invasive procedure. In another embodiment, the first conduit may be coupled to the arterial system without entering the chest cavity or abdominal cavity of the patient, and the pump may be located within the patient, such as superficially, or more invasively, or the pump may be located outside the patient.

A system for supplementing blood flow from the heart of a patient and providing counterpulsation blood flow comprises a first conduit configured to be directed into the left side of the heart, a second conduit configured to be coupled to the arterial system of the patient, and a continuous pump configured to be connected with the first and second conduits. A third conduit is configured to be coupled to the arterial system of the patient. A pulsatile pump is configured to be connected with the third conduit. At least one power supply is coupled to the pumps. At least one control operates the continuous pump to suction blood from the left side of the heart through the first conduit and expel blood from the continuous pump into the second conduit and the arterial system, and operates the pulsatile pump to suction blood from the arterial system through the third conduit while the heart is in systole and expel the blood from the pulsatile pump into the arterial system while the heart is in diastole.

A pulsatile counterpulsation pump for use in assisting the heart of a patient, in accordance with the invention, comprises a pump housing having a chamber and an inlet and an outlet in fluid communication with the chamber. A movable member is mounted in the housing and suctions blood into the inlet and expels blood from the outlet in a pulsatile manner. A flushing fluid inlet communicates with the chamber for introducing a flushing fluid into the chamber and reducing blood clotting.

In another embodiment, a pulsatile counterpulsation pump includes a pump housing having a chamber and an inlet and an outlet in fluid communication with the chamber. A movable member is mounted in the housing and suctions blood into the inlet in a first stroke and expels blood from the outlet in a second stroke. The chamber may be evacuated of at least substantially all blood at the end of the second stroke, for example, by use of the movable member itself, through the use of a separate element from the movable member, or a combination of both.

Various additional features and advantages of the invention will become more readily apparent to those of ordinary skill in the art upon review of the following detailed description of various illustrative examples, taken in conjunction with the accompanying drawings.

DETAILED DESCRIPTION OF THE ILLUSTRATIVE EMBODIMENTS

Figure 1:
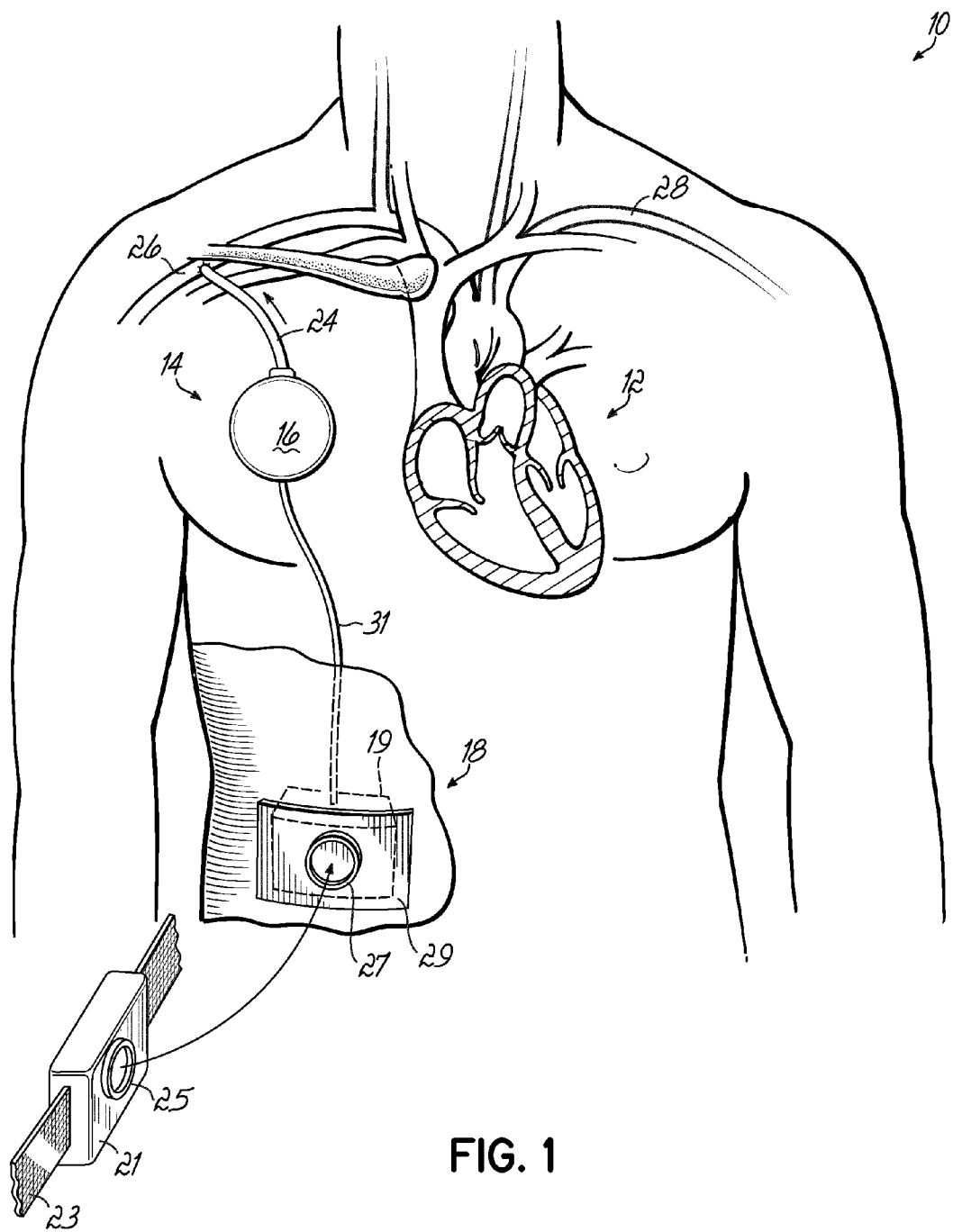
FIG. 1 is a schematic view of a patient with a counterpulsation system installed including a superficially implanted pump to pump blood to and from a shoulder artery.

In each of the systems described below, blood is removed from the patient's arterial blood system during systole and pumped back into the blood system during diastole. In the various figures, like reference numerals refer to like structure, while like reference numerals with prime marks (') refer to corresponding elements that have been modified in manners that will be apparent or described.

FIG. 1 illustrates a patient 10 having a heart 12, shown in longitudinal cross section, coupled with a supplemental assist device or system 14. System 14 comprises a pulsatile pump device 16 which may be implanted in a small pocket made subcutaneously over the patient's chest, such as in the subclavicular region as shown in the drawing. This is a similar implantation procedure to conventional pacemakers. Pump 16 is coupled with a control. Power supply 18 may be an implanted power supply or a power supply partially or wholly external to the patient. One particularly desirable power system comprises a transcutaneous power supply using a power coil which is periodically charged from outside the body to continuously operate pump 16. This system is discussed further below. Pump 16 is coupled with a catheter or conduit 24 which is connected for fluid communication with a superficial artery 26 in the shoulder region.

As further illustrated in FIG. 1, power supply 18 most preferably comprises a first coil or power supply portion and a driver unit. Preferably, the driver unit is a fluid driven unit such as a hydraulic unit 19 which has a compliance chamber (not shown) for storing hydraulic fluid. Hydraulic unit 19 is implanted within the body of patient 10, such as in the lower abdominal region, and a second coil or power supply portion 21 is positioned outside the patient's body. Second coil 21 may be in the form of a pack carried on a belt 23 worn by patient 10. Second coil 21 includes a first alignment element 25 and a second alignment element 27 is carried by an adhesive pad 29 affixed to the skin of patient 10. As further shown in FIG. 1, a conduit 31 is connected between driver unit 19 and pump 16 for supplying pressurized air or liquid, such as helium or saline solution, to operate pump 16 as described further below. In various figures below, the power supply and other control components may be deleted solely for clarity.

Figure 2A:
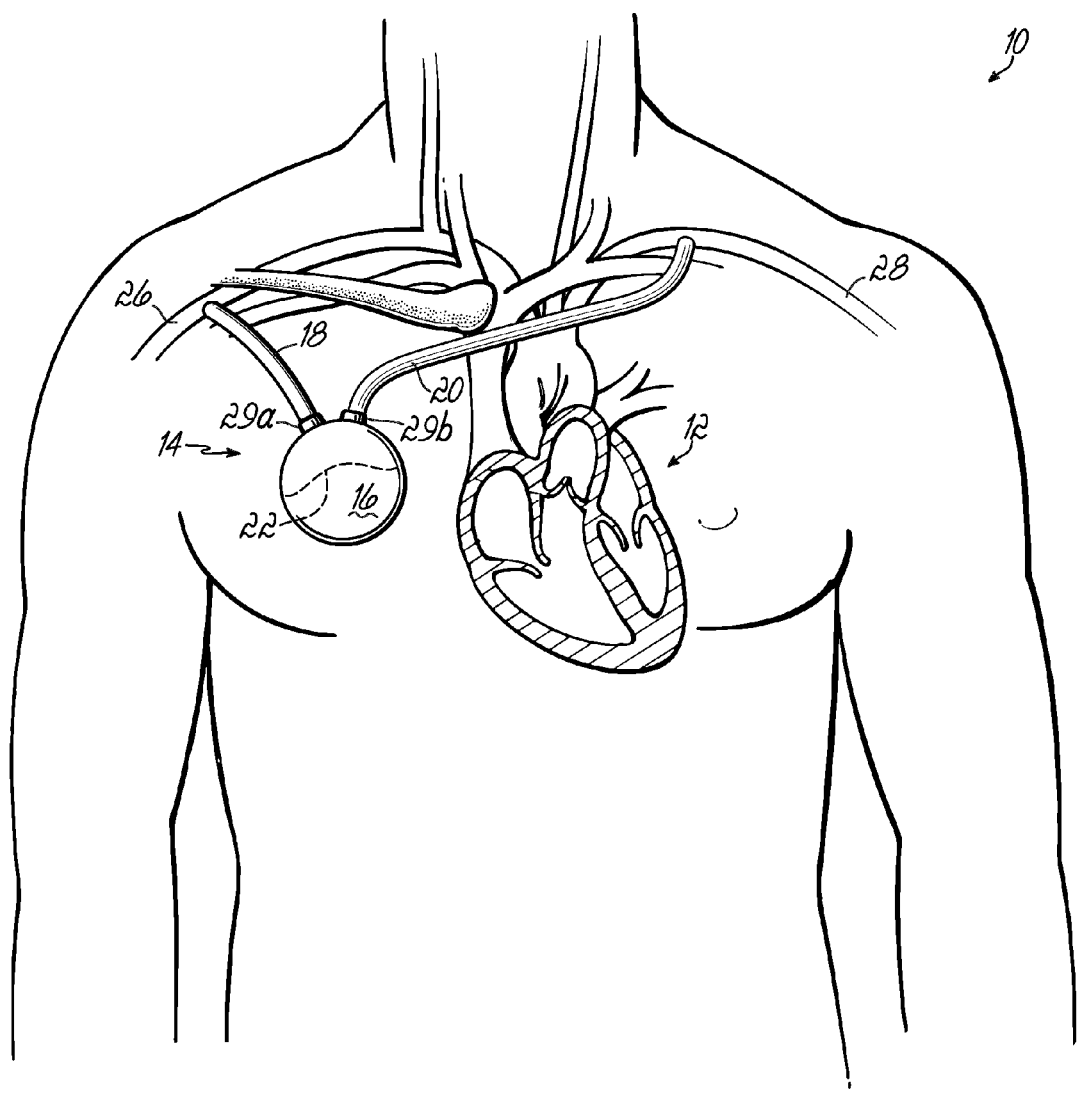
FIG. 2A is a schematic view of an alternative embodiment including two conduits coupled to the superficially implanted pump to pump blood to two different shoulder arteries.

FIG. 2A illustrates a system similar to that shown in FIG. 1, but illustrating the pump 16 as being external to the patient and connected via two conduits 18, 20 simultaneously to two different superficial arteries 26, 28. A movable member 22, such as diaphragm or bladder is shown in pump 16 and moves back and forth to suction blood into the pump 16 and expel blood from the pump via both conduits 18, 20. Alternatively, check valves 29a, 29b may be used to cause blood to be suctioned into pump 16 via one of conduits 18, 20 and expelled from pump 16 via the other of conduits 18, 20.

Figure 2B:
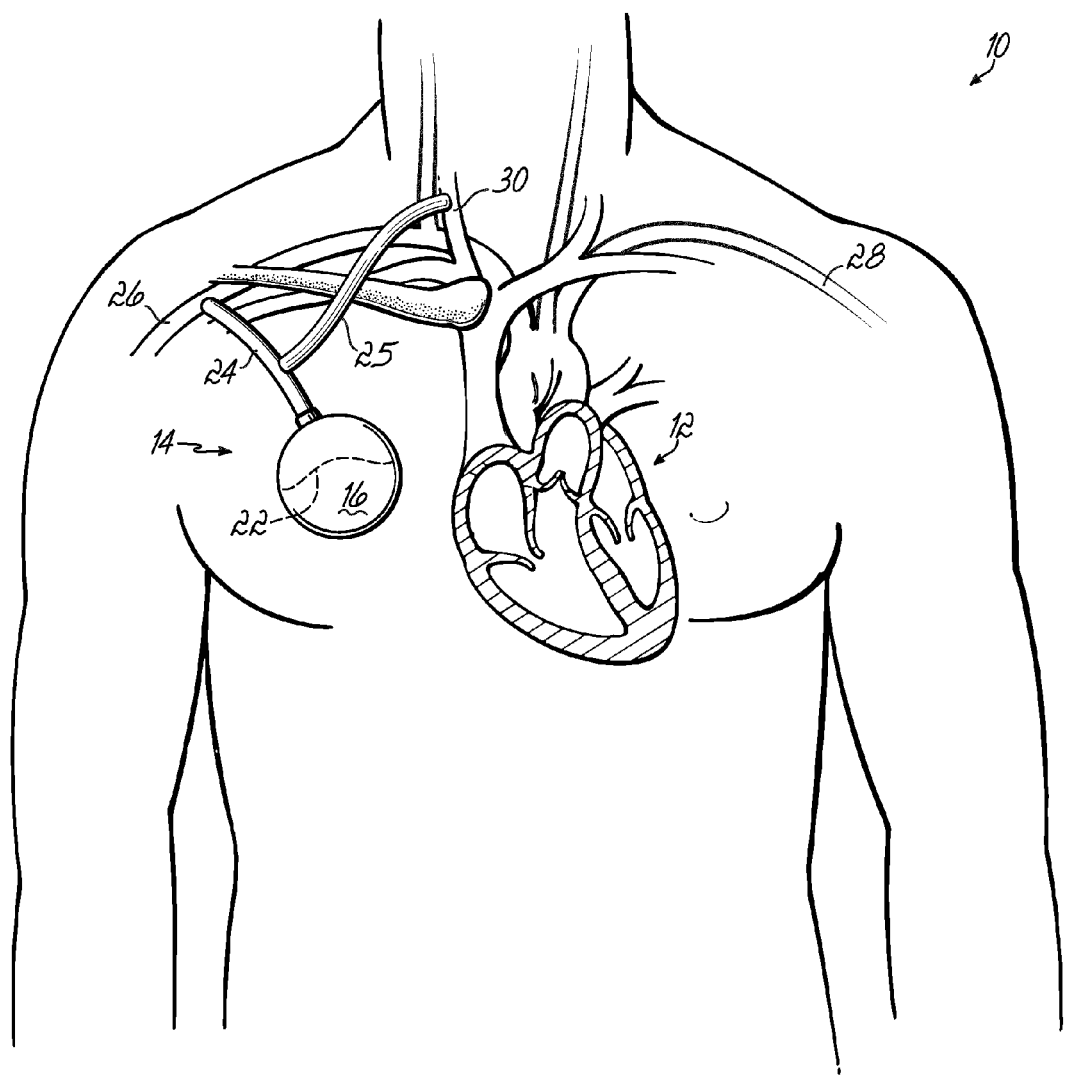
FIG. 2B is a schematic view of another alternative superficially implanted counterpulsation system installed into a patient.

FIG. 2B illustrates a system similar to FIG. 2A but illustrating an alternative connection of blood flow conduits 24, 25 between two different arteries 26, 30 and the pump 16.

Figure 2C:
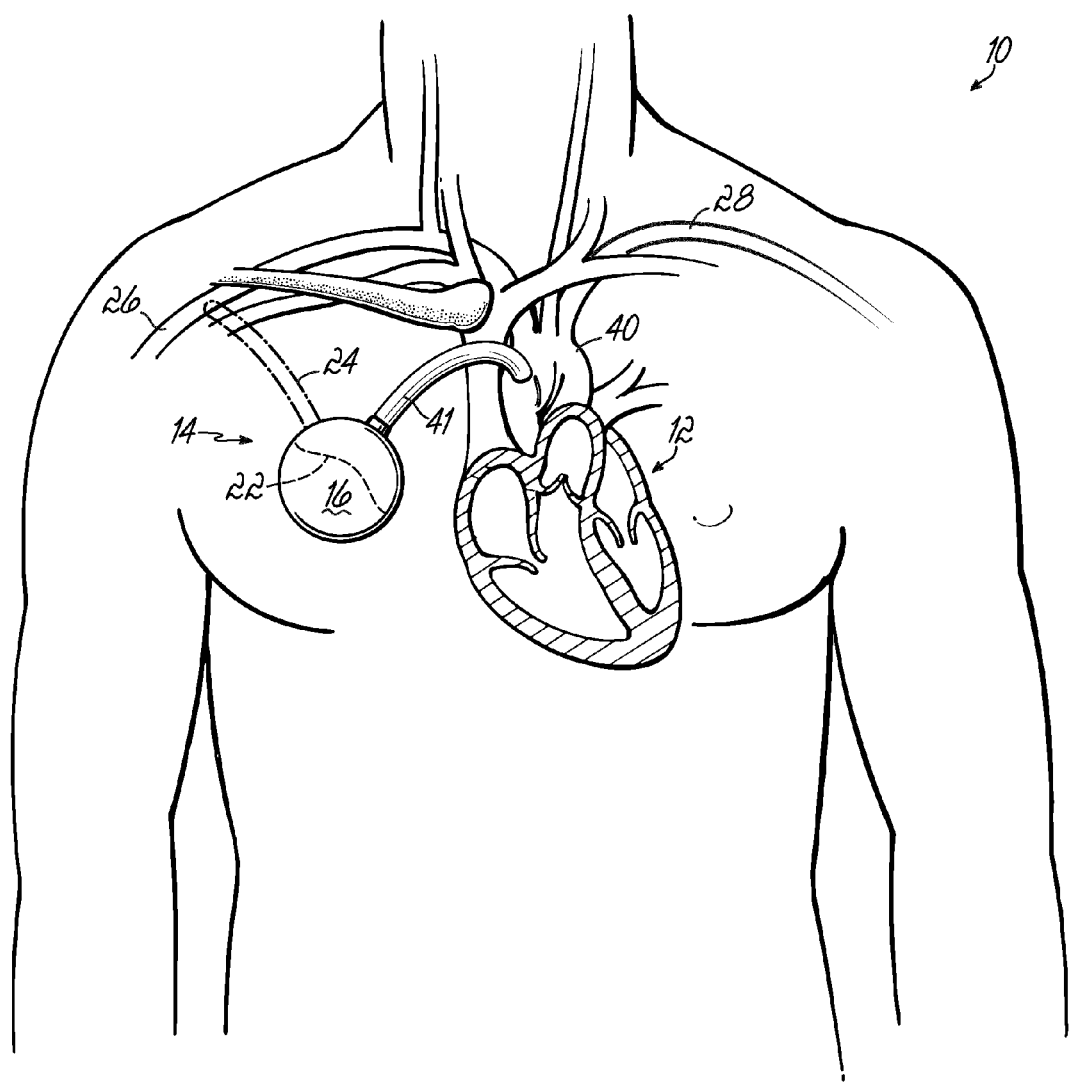
FIG. 2C is a schematic view of another alternative system installed into a patient.

FIG. 2C illustrates another alternative similar to FIGS. 2A and 2B, but illustrating another alternative connection between the pump 16 and the aorta 40 via a conduit 41.

Figure 2D:
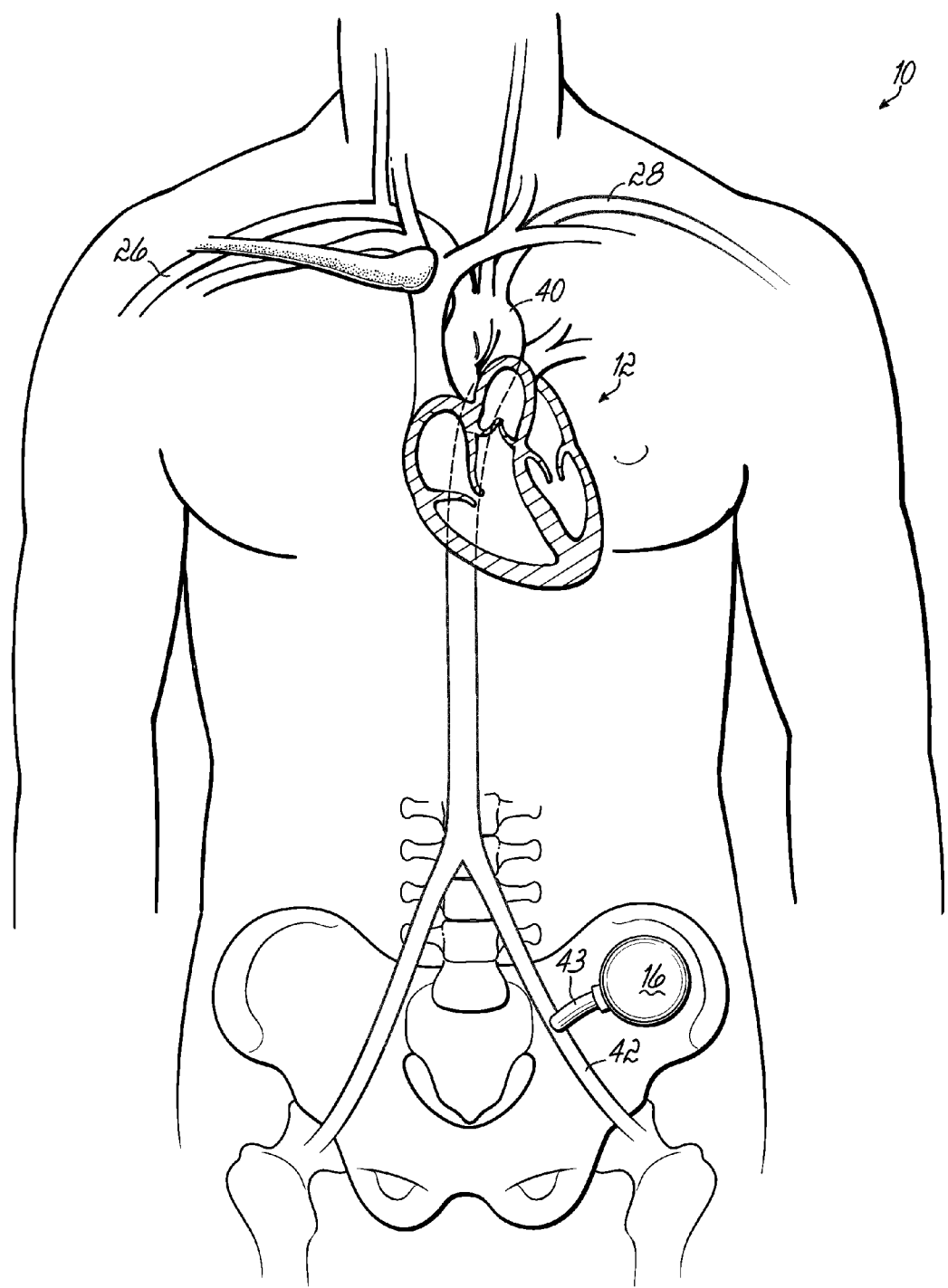
FIG. 2D is another alternative embodiment of a system installed into the groin area of a patient.

FIG. 2D illustrates another possible configuration in which the pump 16 is implanted in the pelvic or groin region by performing a less invasive procedure which is much less traumatic for the patient than intrathoracic or intraabdominal procedures. In this embodiment, an artery 42 in the groin region is coupled to at least one conduit 43 which is coupled to the pulsatile pump 16. Possible arteries utilized in this region of the body are the distal aorta, iliac, external iliac, internal iliac or femoral arteries. The pump 16 can be implanted in a superficial, subcutaneous pelvic area of the body, or in a retroperitoneal location or other pelvic area location.

Figure 3:
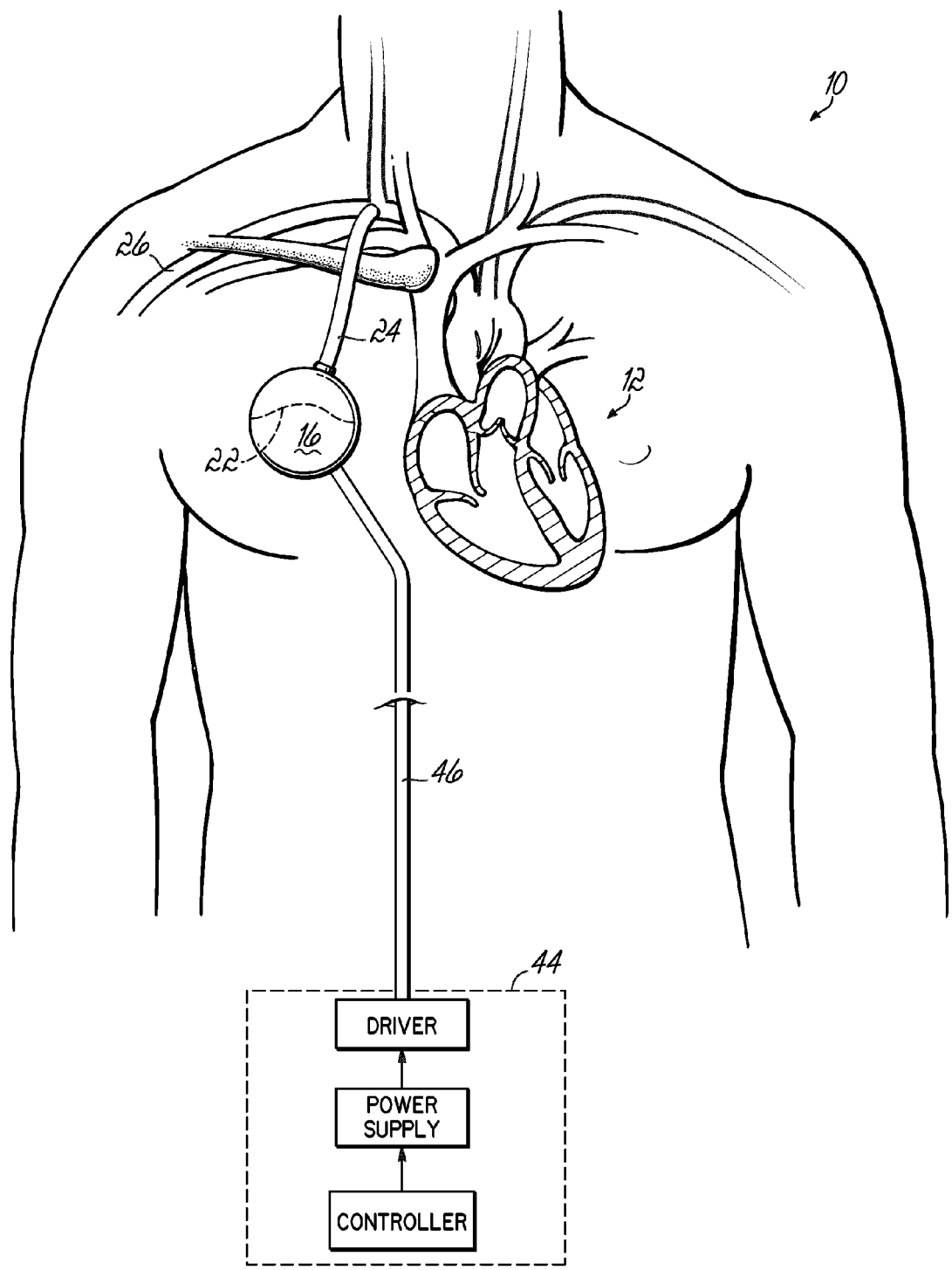
FIG. 3 is a schematic view of a system similar to that shown in FIG. 1 and including a schematic view of a control system and drive system for the pump.

FIG. 3 illustrates a system similar to those described above, but further illustrating a schematic control system 44 including a controller, power supply and driver. The driver may, for example, be a pneumatic or hydraulic device which delivers fluid such as pressurized air or liquid into and out of the pump 16 via conduit 46 to thereby move an element, such as a diaphragm, bladder, pouch or sack 22 back and forth in controlled or coordinated relation to the patient's heartbeat generally as described above in conventional counterpulsation techniques, and using similar control techniques to ensure proper rhythm and timing during systole and diastole.

Figure 4:
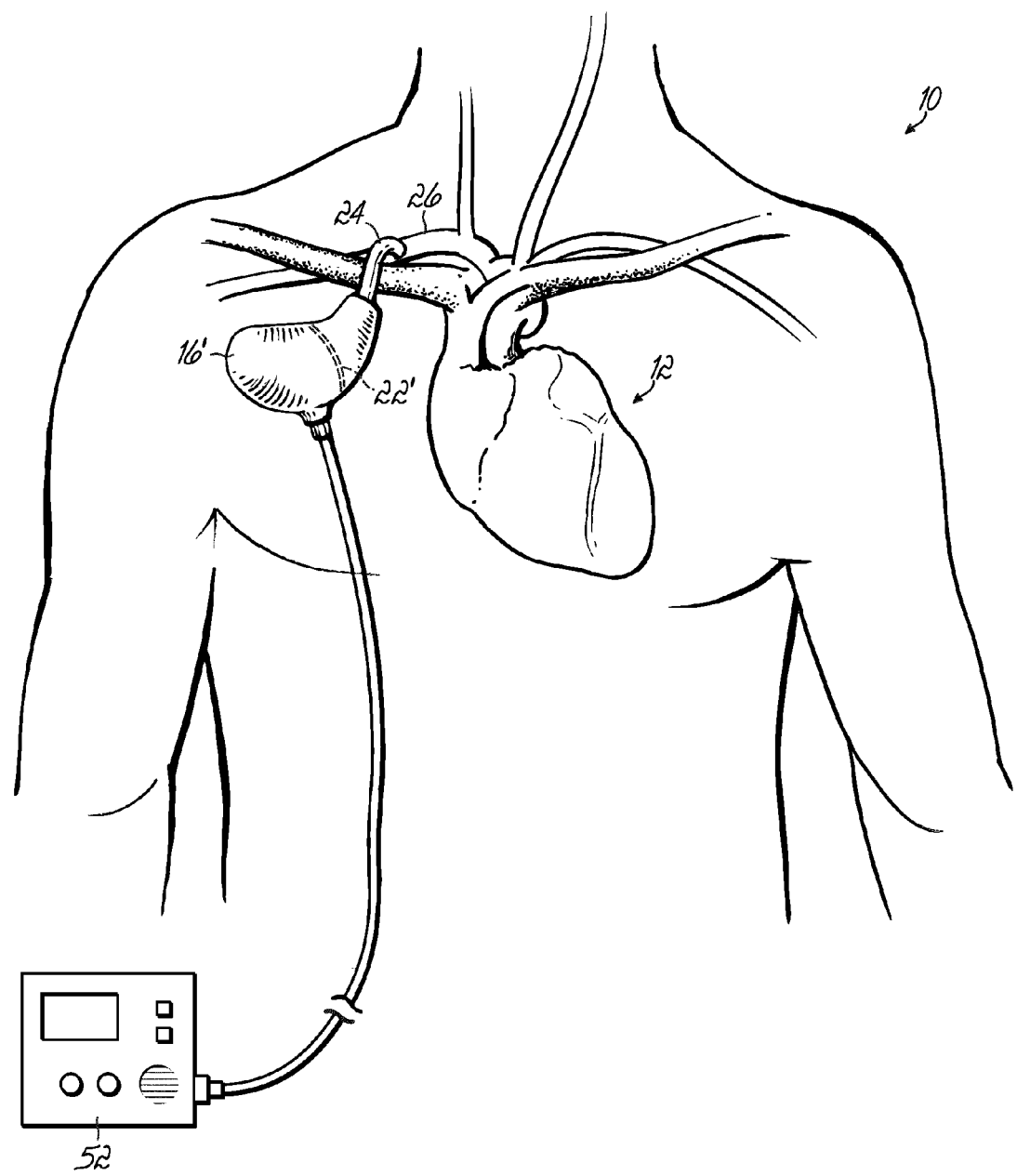
FIG. 4 is a schematic view of another counterpulsation system installed in a patient.

FIG. 4 illustrates an alternative system in which the pump 16' is again external to the patient and is connected to a suitable controller/drive unit 52 for pneumatically or hydraulically moving an internal element 22', such as a diaphragm, bladder, pouch, etc., back and forth and thereby moving blood into and out of the pump 16' and into and out of a superficially located artery 26 via a conduit 24.

Figure 5:
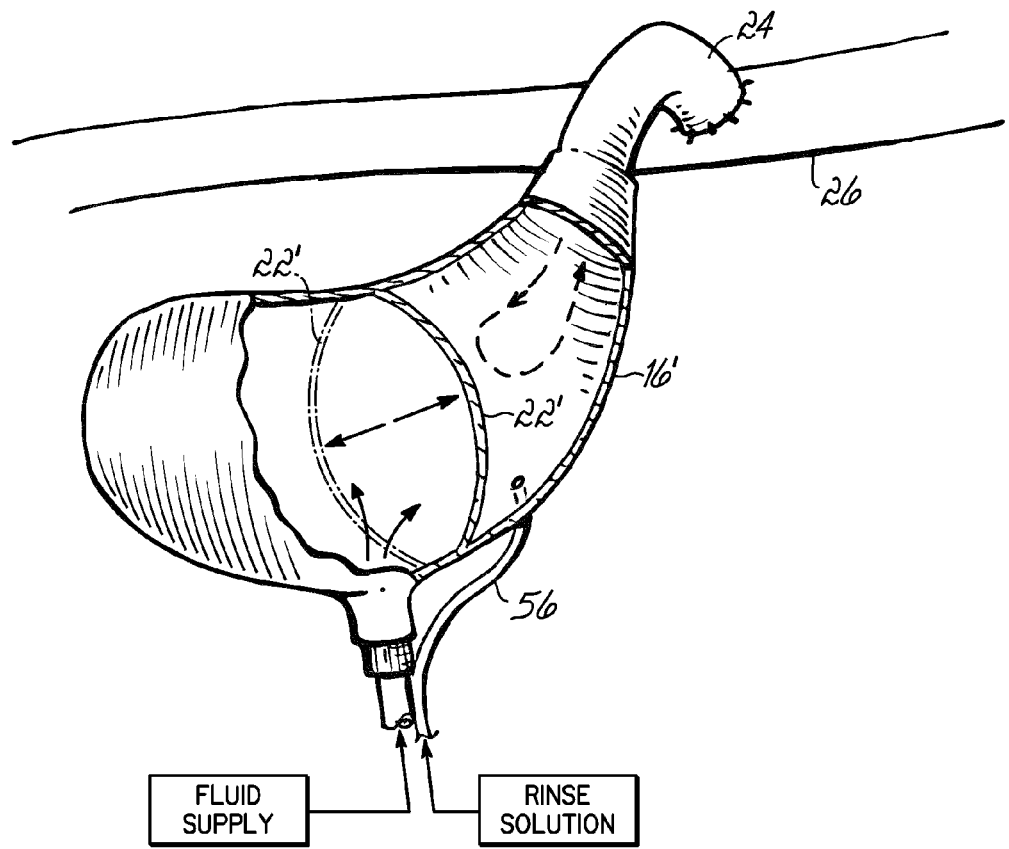
FIG. 5 is an enlarged view of the pump shown in FIG. 4, and fragmented to show certain internal details.

FIG. 5 illustrates an enlarged view of the pump 16' shown in FIG. 4 and, more specifically, showing the bladder 22' moving back and forth through the effects of introduced and exhausted gas or liquid from a fluid supply. Saline or other flushing liquid may be introduced through another conduit 56 for allowing cleaning operations to take place preventing or alleviating blood clots.

Figure 6:
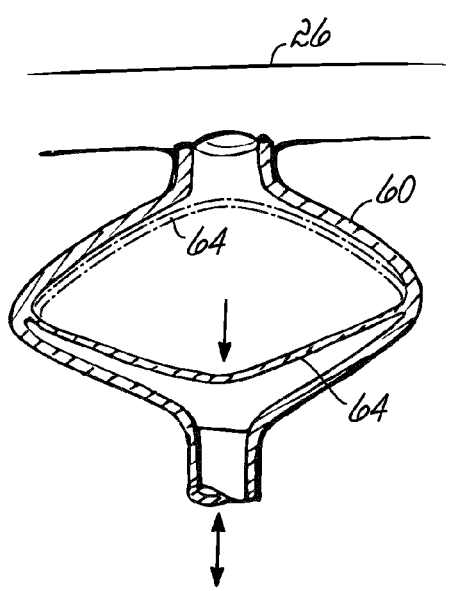
FIG. 6 is a cross sectional view of one form of counterpulsation pump usable in the present invention.
Figure 7:
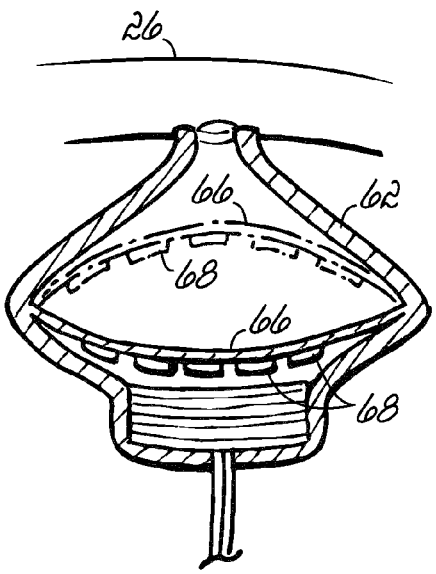
FIG. 7 is a cross sectional view of another alternative embodiment of a counterpulsation pump usable in the present invention.

FIGS. 6 and 7 illustrate two additional alternative pumps 60, 62 with FIG. 6 illustrating another fluid operated bladder 64 which, in the fully activated position shown in phantom lines, either completely or at least substantially fills the entire void within the pump 60 to prevent the possibility of stagnated blood and resulting blood clots. FIG. 7 illustrates the use of an electromagnetic drive which moves the bladder 66 via magnets 68 being attracted to and repelled from an electromagnetic device.

Figure 8:
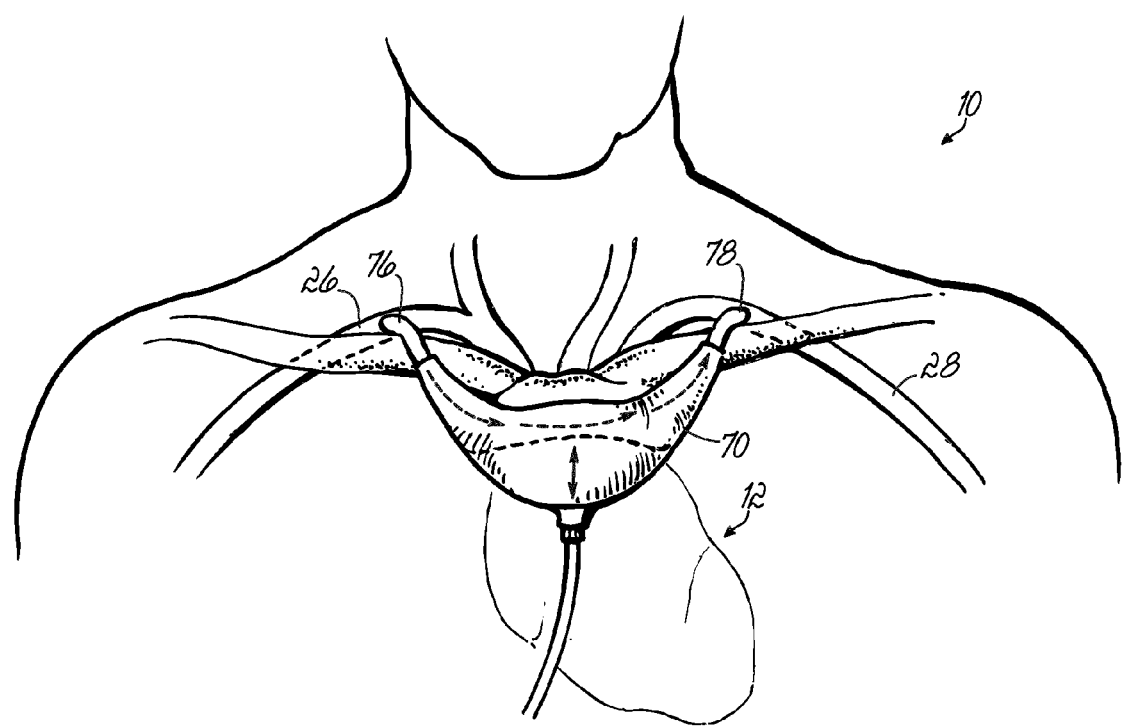
FIG. 8 is a schematic view illustrating another alternative counterpulsation system installed in a patient.

FIG. 8 illustrates another externally positioned counterpulsation pump 70 connected to two different superficial arteries 72, 74 for simultaneously suctioning and expelling blood out of and into arteries 26, 28 via conduits 76, 78.

Figure 9:
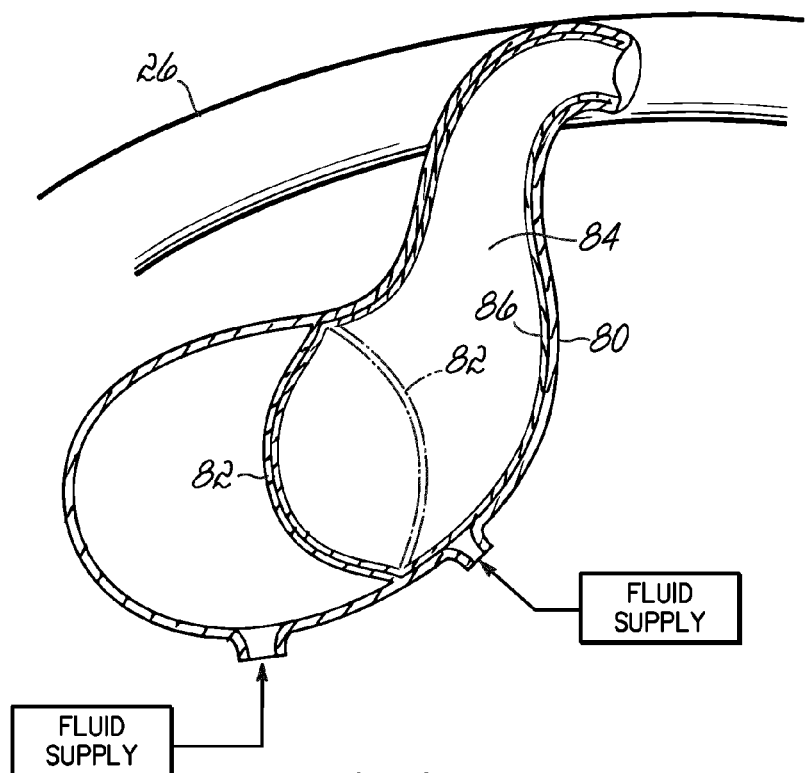
FIG. 9 is a cross sectional view of a pump usable in the present invention and illustrated in cross section to show an internal bladder in an expanded state.
Figure 10:
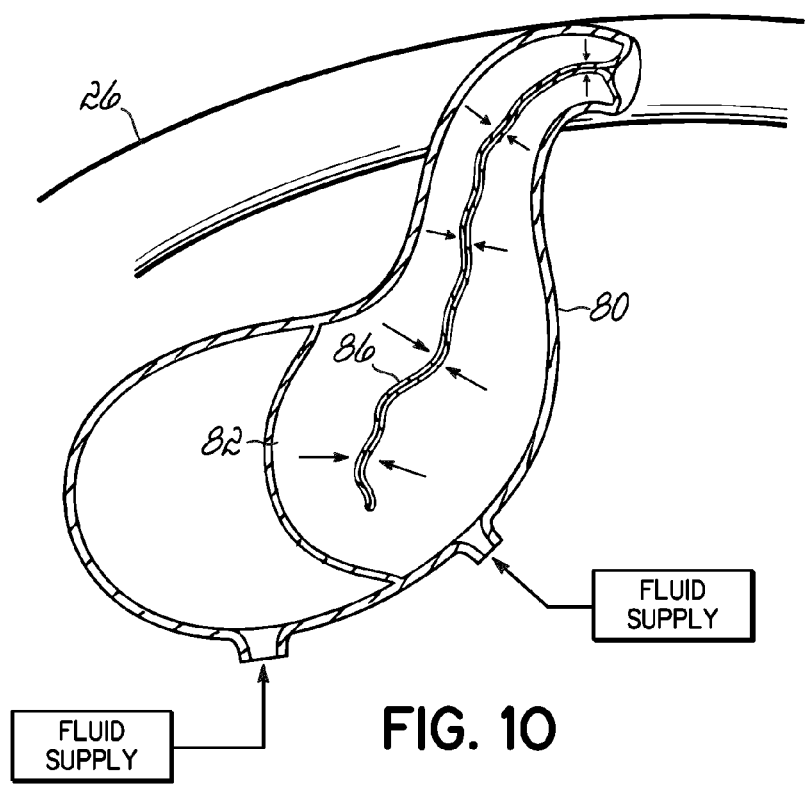
FIG. 10 is a cross sectional view similar to FIG. 9, but illustrating the expandable bladder in a compressed state.

FIGS. 9 and 10 illustrate another embodiment of a counterpulsation pump 80 using a bladder, pouch or sack 82 which is operated by the introduction of pressurized fluid, such as gas or liquid and exhaustion thereof to move bladder 82 back and forth and thereby draw blood into and discharge blood from an internal space 84 within the pump 80. A secondary flexible bladder 86 is connected as shown and may be compressed via the introduction of a pressurized fluid as shown in FIG. 10 to completely expel blood from the internal space 84. This inhibits the formation of blood clots, for example, when the user needs to turn the pump off for any reason. It may also be desirable to have the position shown in FIG. 10 as the normal off position of the system as a fail safe measure should the patient be disconnected from the power supply of the unit.

Figure 11:
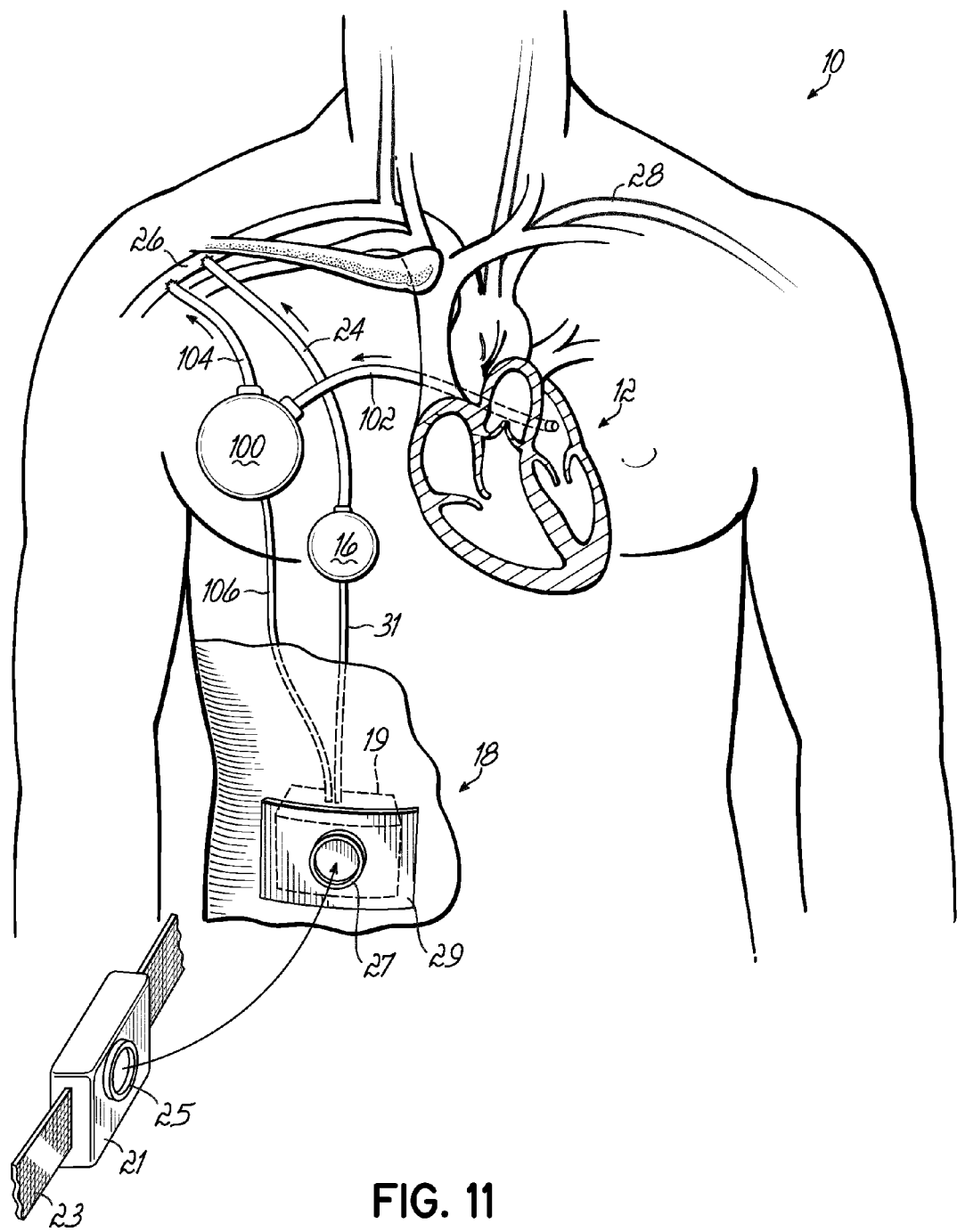
FIG. 11 illustrates another alternative system including both a counterpulsation system and a steady or continuous flow pump system installed in a patient.

It may also be useful to counterpulse in the presence of a heart assist pump 100, particularly if the pump 100 is not pulsatile (steady flow). Such a system is shown in FIG. 11. Coronary perfusion occurs in diastole and by timing counterpulsation pump 16, the flow produced by a constant flow pump 100 can be directed to one or more arteries. Thus, it may be possible to replace a large bulky left ventricular pump with a smaller steady flow pump 100 and a counterpulsation device 16. As further shown in FIG. 11, pump 100 may be a steady flow pump which extracts blood from the left side of the heart 12 through a conduit 102 and expels the blood through a conduit 104 into a superficial artery 26. Pump 100 may be operated by the same control 18 as pump 16, or by any other suitable separate control, and may be a hydraulic, pneumatic or electric pump. The heart assist pump 100 may be comprised of any desired internal, external or combined internal/external pump system suited to the particular patient.

While the present invention has been illustrated by the description of the various embodiments thereof, and while the embodiments have been described in considerable detail, it is not intended to restrict or in any way limit the scope of the appended claims to such detail. Additional advantages and modifications will readily appear to those skilled in the art. The invention in its broader aspects is therefore not limited to the specific details, representative apparatus and methods and illustrative examples shown and described. Accordingly, departures may be made from such details without departing from the scope or spirit of Applicant's general inventive concept.

What is claimed is:

1. A counterpulsation method of assisting the heart of a patient using a pump assist system, the method comprising:
   coupling a first conduit to the cardiovascular system in the chest cavity of the patient,
   connecting a first port of a pulsatile pump to the first conduit,
   implanting the pump in the patient outside of the chest cavity and outside of the abdominal cavity of the patient,
   connecting a driver unit to the pump, and
   coordinating the operation of the pulsatile pump with the driver unit to suction blood from the cardiovascular system through the first port and the first conduit while the heart is in systole and expel the blood into the first port and the first conduit and the cardiovascular system while the heart is in diastole wherein operation of the pump includes delivering a fluid from the driver unit to the pump.

2. The method of claim 1, further comprising:
   affixing the driver unit to the patient at a location outside the body of the patient,
   directing the fluid from a location outside the body of the patient to the implanted pump.

3. The method of claim 1, further comprising:
   coupling a driver conduit from the driver unit to an opposite side of the pump relative to the first conduit, and
   supplying the fluid to the pump through the driver conduit.

4. The method of claim 1, further comprising implanting the pump in a superficial, subcutaneous area of the patient.

5. The method of claim 1, further comprising:
   implanting the driver unit in the patient.

6. The method of claim 5, further comprising:
   implanting a power supply in the patient, and
   supplying power to the pump with the power supply.

* * * * *